United States Patent [19]

Merten et al.

[11] 4,297,269

[45] Oct. 27, 1981

[54] N,N'-BIS(1-CYCLOHEXYL-1-ETHYL)-P-PHENYLENEDIAMINE, AND RUBBER COMPOUNDS CONTAINING THE SAME

[75] Inventors: Helmut L. Merten, Hudson; Gene R. Wilder, Medina, both of Ohio

[73] Assignee: Monsanto Company, St. Louis, Mo.

[21] Appl. No.: 197,400

[22] Filed: Oct. 16, 1980

[51] Int. Cl.³ ........................ C08K 5/18; C07C 87/38
[52] U.S. Cl. ............................ 260/45.9 QB; 260/809; 564/306
[58] Field of Search ................ 564/306; 260/45.9 QB, 260/809

[56] References Cited

U.S. PATENT DOCUMENTS 3,163,616  12/1964  Stahly ................................ 260/45.9
3,511,805   5/1970  Kosmin et al. ..................... 260/45.9

*Primary Examiner*—V. P. Hoke
*Attorney, Agent, or Firm*—Gordon B. Seward

[57] ABSTRACT

N,N'-Bis(1-cyclohexyl-1-ethyl)-p-phenylenediamine is disclosed as a novel compound, useful as an antidegradant for organic materials, such as rubber. Vulcanized or vulcanizable rubber compounds containing minor amounts of this compound show excellent resistance to ozone attack, under static or dynamic exposure.

8 Claims, No Drawings

N,N'-BIS(1-CYCLOHEXYL-1-ETHYL)-P-PHENYLENEDIAMINE, AND RUBBER COMPOUNDS CONTAINING THE SAME

BACKGROUND OF THE INVENTION

This invention relates to dicycloalkyl-p-phenylenediamines and to their use in vulcanized or vulcanizable rubber as a preservative or antidegradant.

N,N'-substituted p-phenylenediamine compounds have found extensive use in rubber compounds as antidegradants. Especially in protection against ozone attack these compounds have been shown to be very effective. When incorporated into vulcanizable rubber at a level of from 0.1 to 5 percent by weight, based on the weight of the rubber, their use is effective in preventing surface cracking of rubber articles, even in such extreme service conditions as are encountered in pneumatic tire sidewalls. There, the continual flexing action renders other protection methods (such as incorporation of wax in the rubber compound) relatively ineffective. While wax offers protection against ozone in static use, the presence of wax in a rubber compound can actually have a negative effect on dynamic ozone resistance.

Many N,N'-substituted p-phenylenediamine compounds have been suggested for this use, and a number have found widespread acceptance in the rubber industry. Some of these compounds, however, are relatively expensive or difficult to prepare, exhibit skin-sensitizing behavior, or are in a form so as to be difficult to handle in the rubber mixing operations.

SUMMARY OF THE INVENTION

In accordance with this invention, it has now been found that a novel compound having the formula N,N'-bis(1-cyclohexyl-1-ethyl)-p-phenylenediamine is particularly effective as an antidegradant in organic materials susceptible to oxygen attack, especially in vulcanizable or vulcanized rubber. Vulcanized or vulcanizable rubber compounds incorporating the compound of the invention, at a level of from 0.1 to 5.0 parts by weight per 100 parts of rubber by weight, show resistance to ozone attack.

One of the starting materials in the preferred method for preparing the compound of the invention is acetophenone, a material of commerce, which is readily available as a by-product of the manufacture of other chemicals.

DESCRIPTION OF THE PREFERRED EMBODIMENTS

In a preferred method, the compound of the invention can be prepared by first hydrogenating acetophenone to produce 1-hydroxyethylcyclohexane, oxidizing that compound to produce cyclohexyl methyl ketone, and then reacting the ketone with p-nitroaniline by means of reductive alkylation to produce N,N'-bis(1-cyclohexyl-1-ethyl)-p-phenylenediamine. This preferred preparation is described in detail in the following examples.

EXAMPLE I

Preparation of 1-hydroxyethylcyclohexane

Into a 1-liter stainless steel autoclave (Parr, series 4500) equipped with an agitator, coils for heating and cooling, appropriate inlets and outlets, pressure gage and rupture disc, were charged 360 g. (3.0 mole) of acetophenone and 10 g. of 5% rhodium on alumina (Engelhard Ind.). Air was removed from the autoclave by purging twice with nitrogen up to 0.69 MPa.

The contents were heated to 100°–110° C. and 2.8 MPa of hydrogen pressure was placed on the contents, replacing the hydrogen by fresh hydrogen as it was absorbed. After an hour, the temperature was raised to 150° C. and the reaction was allowed to continue until no more hydrogen was apparently being absorbed. The excess gas was then vented, the autoclave was opened and the catalyst was removed from the product by filtration.

The product was purified by distilling twice under 0.013 MPa absolute pressure and collecting the fraction boiling at 126°–130° C. There was obtained 210 g. of product, representing a yield of 54.7%, which had a refractive index of 1.472.

EXAMPLE II

Preparation of Cyclohexyl Methyl Ketone

Into a two-liter, round bottom, three-necked flask equipped with a condenser, a mechanical stirrer, thermometer and a liquid addition funnel were placed 900 ml. of water, 200 g. (0.67 mole) of technical grade sodium dichromate followed by 176 g. (1.8 mole) of concentrated sulfuric acid. The contents were cooled to 55°–60° C. and 120 g. (0.94 mole) of 1-hydroxyethylcyclohexane was added over a period of 1 hour, holding the temperature between 55°–50° C. by means of external cooling. After the alcohol had been added, the reaction mixture was allowed to stir for an additional 30 minutes and then 600 ml. of water was added and the contents heated to remove the ketone by steam distillation. When no more ketone was being steam distilled, the heat was removed, the distillate of water and ketone separated and the upper organic layer was distilled under vacuum collecting the fraction boiling at 115°–116° C. There was obtained 76 g. of ketone representing a 64% yield.

EXAMPLE III

Preparation of N,N'-Bis(1-cyclohexyl-1-ethyl)-p-phenylenediamine

Into a 1-liter stainless steel autoclave (Parr, series 4500) equipped with an agitator, coils for heating and cooling, appropriate inlets and outlets, pressure gage and rupture disc, were charged 55 g. (0.4 mole) of para-nitroaniline, 126 g. (1.0 mole) of cyclohexyl methyl ketone, 100 g. of mixed xylene, 6 g. of 1% platinum on carbon and 6 g. of Nuchar C-100 carbon. The vessel was purged with nitrogen twice to 0.69 MPa and vented. The contents of the autoclave were heated to 100° C. and 1.38 MPa of hydrogen pressure was placed on the contents. After the nitro group had been reduced (as noted when the reaction was no longer exothermic) the hydrogen pressure was raised to 2.66 MPa and the temperature was raised to 150° C. The contents were reacted at these conditions for 1 hour and then the reactor was cooled and the excess gas vented. The autoclave was opened and its contents were filtered to remove the catalyst. The excess ketone and xylenes were removed under about 0.00066 MPa pressure at a maximum temperature of 160° C. and the residue was the product. There was obtained 97 g. (74% yield) of oily product. The product solidified on standing and a sample crystallized from petroleum ether showed a melting point of 55°–56° C., and was capable of convenient handling as a solid at room temperature.

An alternative method for making the compound of the invention also starts with acetophenone. After hydrogenation over a catalyst of rhodium on alumina to produce 1-hydroxy-1-ethylcyclohexane, the latter compound is dehydrogenated at 200°–250° C. over a nickel catalyst to acetocyclohexane which in turn is reacted with p-nitroaniline and hydrogen over a platinum-on-carbon catalyst to produce the compound of the invention.

In general, the novel antidegradant compound of this invention is valuable for the preservation of sulfur-vulcanizable diene rubbers. Those rubbers containing more than 50% diene hydrocarbon are preferred. The group of rubbers includes natural rubbers, styrene-butadiene copolymer rubber and the various stereospecific polymerized dienes, for example, cis-polybutadiene and cis-polyisoprene. The composition are also useful in diene rubbers of low unsaturation such as butyl rubber and ethylene-propylene-diene terpolymer rubber (EPDM). The amount to use will vary depending upon the particular formulation and the purpose of the compounder but, in general, the amounts will fall within the range of 0.1 to 5% by weight of the rubber content.

Stereospecific rubbers are normally obtained as cements and it is important to add antidegradant to the organic solvent solution immediately after polymerization has been completed because these rubbers deteriorate rapidly unless adequately protected immediately after polymerization. The new antidegradants are also suited for addition to latex, for example, to protect the rubber phase of SBR rubber latex.

Rubber ozone resistance data for the products of this invention are illustrated by a method published by Decker and Wise, The Stress Relaxation Method for Measuring Ozone Cracking, *Rubber World*, April 1962, page 66. The equipment comprises an oven serving as an ozone cabinet filled with ozone generating equipment and racks for both static and dynamic testing. Static racks handle stocks at strains of 5, 10, 20, 30, and 40%. The dynamic rack is a reciprocal mechanism which imparts a 25% strain to the rubber test piece on movement of a top plate which moves vertically with respect to a stationary bottom plate. The mechanism is driven at a rate of 90 cycles per minute by a gear mounted on the outside of the cabinet. The test pieces are 5 cm. long T-50 (ASTM D599-55) specimens died from standard stress strain test sheets (ASTM D15-57T). They are mounted by placing the ends in radial slots milled into the edges of circular plates of the racks. The tab ends fit into circumferential grooves machined into the outer surfaces of the plates.

The stress relaxation method is based on the principle that the effective cross-sectional area of a small test piece of rubber is reduced by ozone cracking. The extent of cracking in a test piece is determined by measuring the forces required to extend the test piece 100% before and after exposure to ozone. The ozone concentration for the test is 25 parts ozone/100 million parts air. As the strip begins to crack, the number of stress-supporting rubber chains decreases and the force required to extend the strip 100% is reduced. The ratio of this force to the original force is calculated at approximately 16-hour intervals of exposure to ozone. The graph of force vs. time is essentially a straight line and the time required for obtaining 90%, 80% and 70% respectively of the original force is determined from the graph. The ability of the rubber to resist ozone attack is evaluated by comparison of these times to times for suitable controls to reach corresponding percent of the original force. The percents of original moduli of the rubber test pieces are listed as percent retention in Tables III and V infra, and the times to reach those retentions are recorded. Longer times indicate better ozone resistance of the rubber stock. The intermittent test comprises 2-hour cycles during which the specimens are exposed dynamically 15% of the time and during the remainder of the time are exposed statically at 25% strain.

The test stock comprises a typical formulation for the sidewall of a radial pneumatic tire. Most of the ingredients are combined in a Banbury mixer to form a masterbatch. The remaining ingredients are then added to the masterbatch on a mixing mill. On the basis of 100 parts by weight of rubber, the formulation comprises the ingredients and amounts by weight as set forth in Table 1, following.

TABLE 1

| MASTERBATCH | |
|---|---|
| Natural Rubber, SMR-5CV | 50 |
| Polybutadiene Rubber | 50 |
| Carbon Black, N-326 | 50 |
| Processing Oil | 10 |
| Zinc Oxide | 3 |
| Stearic Acid | 1 |
| Wax | 2.5 |
| Total Masterbatch | 166.5 |
| COMBINED ON THE MILL | |
| Masterbatch | 166.5 |
| Sulfur | 2.0 |
| Accelerator, N-t-butyl-2-benzothiazolesulfenamide | 1.0 |
| Antidegradant (if present) | 2.0 |

All stocks were vulcanized at 153° C. for a length of time equal to t90 in the Rheometer data, defined as the time to reach a torque equal to the minimum torque plus 0.9 times the difference between the minimum and maximum torque. In this way, the degree of cure of all stocks is essentially the same. The different stocks contained the antidegradants identified in Table II, following.

TABLE II

| LEGEND OF ANTIDEGRADANTS | |
|---|---|
| Stock | Structure |
| 1 | Blank |
| 2 | CH₃−CH(CH₃)−CH₂−CH(CH₃)−NH−C₆H₄−NH−C₆H₅ |
| 3 | CH₃−CH(CH₃)−CH₂−CH₂−CH(CH₃)−NH−C₆H₄−NH−CH(CH₃)−CH₂−CH₂−CH(CH₃)−CH₃ |

TABLE II-continued
LEGEND OF ANTIDEGRADANTS

| Stock | Structure |
|---|---|
| 4 | 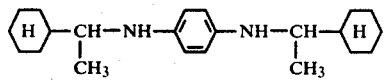 |
| 5 | 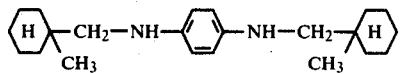 |
| 6 | 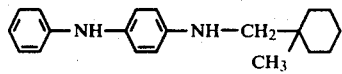 |
| 7 | 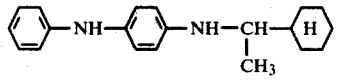 |

Antidegradants 2 and 3 are commercial antiozonants. Antidegradant 4 is the compound of the invention. Antidegradants 5 and 6 are suggested in U.S. Pat. No. 3,511,805, and antidegradant 7 is shown in U.S. Pat. No. 3,163,616.

Samples of each stock were prepared and tested for ozone resistance as described above. The results of the tests are set forth in Table III following.

The data in Table III show, generally, that the aged ozone exposure was too severe a test to discriminate differences among the antidegradants. The unaged results show that the compound of the invention, contained in Stock 4, performed significantly better than that of Stock 5, and as well as, or better than, Stocks 6 and 7. Although the results for Stocks 2 and 3, the commercial antidegradants, were superior, in general, to Stock 4, if the higher molecular weight of the compound of the invention is taken into consideration, the results are comparable, if not equivalent. A dash indicates the sample failed before reaching the indicated percentage of the initial modulus.

In another comparison series, using the same compound formulation, stocks were prepared containing the antidegradants set forth in Table IV, following.

It should be observed that Stocks 1, 2, 3, 4, and 7 contain the same antidegradants as their counterparts in Table II, above, while Stocks 5 and 6 contain other antidegradant compounds shown in U.S. Pat. No. 3,511,805.

Samples of each stock were prepared and tested for ozone resistance as before. The test results are set forth in Table V following.

TABLE III

| | Stock | | | | | | |
|---|---|---|---|---|---|---|---|
| | 1 | 2 | 3 | 4 | 5 | 6 | 7 |
| Unaged dynamic ozone resistance: | | | | | | | |
| 90% retention, hours | 2 | 24 | 26 | 15 | 5 | 11 | 14 |
| 80% retention, hours | 4 | 37 | 35 | 25 | 12 | 21 | 26 |
| 70% retention, hours | 6 | 47 | 41 | 33 | 18 | 30 | 37 |
| Unaged static ozone resistance: | | | | | | | |
| 90% retention, hours | — | — | 87 | — | — | 193 | — |
| Unaged intermittent ozone resistance: | | | | | | | |
| 90% retention, hours | — | 42 | 27 | 33 | 25 | 26 | 31 |
| 80% retention, hours | — | 55 | 41 | 46 | 31 | 33 | 40 |
| 70% retention, hours | — | — | — | — | 36 | 39 | 47 |
| Aged dynamic ozone resistance: | | | | | | | |
| 90% retention, hours | 2 | 7 | 3 | 2 | 2 | 4 | 6 |
| 80% retention, hours | 4 | 15 | 7 | 5 | 5 | 9 | 12 |
| 70% retention, hours | 7 | 23 | 11 | 8 | 8 | 13 | 19 |
| Aged static ozone resistance: | | | | | | | |
| 90% retention, hours | — | 153 | 23 | — | — | 47 | — |
| Aged intermittent ozone resistance: | | | | | | | |
| 90% retention, hours | — | 26 | 10 | 7 | 6 | 14 | 17 |
| 80% retention, hours | — | 33 | — | 14 | 12 | — | 27 |
| 70% retention, hours | — | 39 | — | — | — | — | — |

TABLE IV
LEGEND OF ANTIDEGRADANTS

| Stock | Structure |
|---|---|
| 1 | Blank |
| 2 | 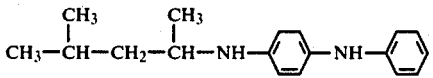 |
| 3 | 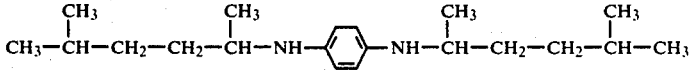 |

TABLE IV-continued
LEGEND OF ANTIDEGRADANTS

| Stock | Structure |
|---|---|
| 4 | (H)—CH(CH₃)—NH—⟨⟩—NH—CH(CH₃)—(H) |
| 5 | (H)—CH₂NH—⟨⟩—NHCH₂—(H) |
| 6 | (H)—CH₂NH—⟨⟩—NH—⟨⟩ |
| 7 | (H)—CH(CH₃)—NH—⟨⟩—NH—⟨⟩ |

TABLE V

| | Stock | | | | | | |
|---|---|---|---|---|---|---|---|
| | 1 | 2 | 3 | 4 | 5 | 6 | 7 |
| Unaged dynamic ozone Resistance: | | | | | | | |
| 90% retention, hours | 1 | 31 | 32 | 24 | 4 | 14 | 16 |
| 80% retention, hours | — | 43 | 40 | 30 | 8 | 40 | 34 |
| 70% retention, hours | — | 59 | 48 | — | 11 | 45 | 54 |
| Unaged static ozone resistance: | | | | | | | |
| 90% retention, hours | all over 80 hours | | | | | | |
| Unaged intermittent ozone Resistance: | | | | | | | |
| 90% retention, hours | 1 | 56 | 45 | 45 | 11 | 27 | 53 |
| Aged dynamic ozone Resistance: | | | | | | | |
| 90% retention, hours | 5 | 18 | 3 | 5 | 4 | 4 | 11 |
| 80% retention, hours | 10 | 27 | 10 | 8 | 8 | 8 | 24 |
| Aged static ozone resistance: | | | | | | | |
| 90% retention, hours | all over 64 hours | | | | | | |
| Aged intermittent ozone Resistance: | | | | | | | |
| 90% retention, hours | — | 32 | 18 | 13 | 5 | 11 | 35 |
| 80% retention, hours | — | 45 | 29 | 21 | 9 | 18 | 46 |

The data in Table V indicate that Stock 4 was clearly superior to Stock 5, and roughly equivalent to Stocks 6 and 7; although Stocks 6 and 7 are generally somewhat better than Stock 4. The static tests were inconclusive.

(While the same recipes were followed for the stocks listed in Table IV as for those in Table II, the results in Table V should not be directly compared with those in Table III, since different lots of polymers and other ingredients were employed.)

In summary, the compound of the invention has been shown to be an especially effective antidegradant in protecting rubber from ozone attack. Rubber stocks containing the compound of the invention exhibit good resistance to ozone in a variety of test modes.

Although the invention has been illustrated by typical examples, it is not limited thereto. Changes and modifications of the examples of the invention herein chosen for purposes of disclosure can be made which do not constitute departures from the spirit and scope of the invention.

The embodiments of the invention in which an exclusive property or privilege is claimed are defined as follows:

1. N,N'-bis(1-cyclohexyl-1-ethyl)-p-phenylenediamine.

2. A vulcanizable rubber compound containing a stabilizing amount of N,N'-bis(1-cyclohexyl-1-ethyl)-p-phenylenediamine.

3. A vulcanized rubber compound containing a stabilizing amount of N,N'-bis(1-cyclohexyl-1-ethyl)-p-phenylenediamine.

4. The compound of claim 2, wherein the N,N'-bis(1-cyclohexyl-1-ethyl)-p-phenylenediamine is present in an amount of from 0.01% to 5% by weight, based on the weight of the vulcanizable rubber.

5. The compound of claim 2, wherein the vulcanizable rubber is selected from the group consisting of natural rubber, synthetic cis-1,4-polyisoprene, cis-1,4-polybutadiene, styrene-butadiene copolymers containing at least 50% butadiene, and mixtures thereof.

6. The compound of claim 3, wherein the N,N'-bis(1-cyclohexyl-1-ethyl)-p-phenylenediamine is present in an amount of from 0.01% to 5% by weight, based on the weight of the vulcanized rubber.

7. The compound of claim 3, wherein the vulcanized rubber is selected from the group consisting of natural rubber, synthetic cis-1,4-polyisoprene, cis-1,4-polybutadiene, styrene-butadiene copolymers containing at least 50% butadiene, and mixtures thereof.

8. The compound of claim 3, which is incorporated into a pneumatic tire.

* * * * *